(12) United States Patent
Okwumabua

(10) Patent No.: US 7,572,457 B2
(45) Date of Patent: Aug. 11, 2009

(54) **USE OF *STREPTOCOCCUS SUIS* 38 KDA POLYPEPTIDE AS AN IMMUNOGEN**

(75) Inventor: Ogi E. Okwumabua, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 60 days.

(21) Appl. No.: 11/395,658

(22) Filed: Mar. 31, 2006

(65) Prior Publication Data

US 2007/0231343 A1 Oct. 4, 2007

(51) Int. Cl.
*A61K 39/09* (2006.01)
*A61K 49/00* (2006.01)
*A61K 39/38* (2006.01)
*A61K 39/00* (2006.01)

(52) U.S. Cl. ............ 424/244.1; 424/9.1; 424/9.2; 424/184.1; 424/185.1; 424/190.1; 424/234.1; 350/300; 350/350

(58) Field of Classification Search ............ 424/244.1, 424/9.1, 9.2, 184.1, 185.1, 190.1, 234.1; 350/300, 350
See application file for complete search history.

(56) References Cited

U.S. PATENT DOCUMENTS 5,612,042 A * 3/1997 Jacobs ............... 424/237.1
2005/0020813 A1 * 1/2005 Masignani et al. ......... 530/350

OTHER PUBLICATIONS

Okwumabua et al. Clincal and Diagnostic Laboratory Immunology, Apr. 2005, p. 484-490.*
Li et al. Infection and Immunity, Jan. 2006, p. 305-312.*
Stedman's Online medical dictionary 27th edition. Definition of neutralizing antibody.*
Abbas et al. Cellular and Molecular Immunology 4th edition, 2000 Chapter 3 p. 56.*
Kristensen et al. The Canadian Journal of Veterinary Research 2004; 68:66-70.*
Stedman's Online medical dictionary 27th edition. Definition of neutralizing antibody, 2000.*
Li, Yuanyi et al.; "Identification of a Surface Protein of *Streptococcus suis* and Evaluation of Its Immunogenic and Protective Capacity in Pigs", *Infection and Immunity*, vol. 74, No. 1, Jan. 2006 (pp. 305-312).
Okwumabua, Ogi et al., "Identification of the Gene Encoding a 38-Kilodalton Immunogenic and Protective Antigen of *Streptococcus suis*", *Clinical and Diagnostic Laboratory Immunology*, vol. 12, No. 4, Apr. 2005 (pp. 484-490).
Okwumabua, Ogi et al., "A polymerase chain reaction (PCR) assay specific for *Streptococcus suis* based on the gene encoding the glutamate dehydrogenase", *FEMS Microbiology Letters*, vol. 218, No. 1, Jan. 21, 2003 (pp. 79-84).
Okwumabua, Ogi et al., "Cloning and Characterization of the Gene Encoding the Glutamater Dehydrogenase of *Streptococcus suis* Serotype 2", *Clinical and Diagnostic Laboratory Immunology*, vol. 8, No. 2, Mar. 2001 (pp. 251-257).
Okwumabua, Ogi et al., "Hybridization Analysis of the gene encoding a hemolysin (suilysin) of *Streptococcus suis* type 2: evidence for the absence of the gene in some isolates", *FEMS Microbiology Letters*, vol. 181, No. 1, Dec. 1, 1999 (pp. 113-121).
Okwumabua, Ogi et al., "Detection of Genomic Heterogeneity in *Streptococcus suis* Isolates by DNA Restriction Fragment Length Polymorphisms of rRNA Genes (Ribotyping)", vol. 33, No. 4, *Journal of Clinical Microbiology*, vol. 33, No. 4, Apr. 1995 (pp. 968-972).
Staats, J.J. et al., "*Streptococcus suis*: Past and Present", *Veterinary Research Communications*, vol. 21, No. 6, Aug. 1997 (pp. 381-407).

* cited by examiner

*Primary Examiner*—Rodney P. Swartz
(74) *Attorney, Agent, or Firm*—Foley & Lardner LLP

(57) ABSTRACT

Disclosed are methods, compositions, and kits for inducing polyclonal antibodies against one or more pathogens that include *Streptococcus suis*. The methods may include administering to an animal a composition that includes an isolated 38 kDa polypeptide of *Streptococcus suis* and a suitable excipient. The methods, compositions, and kits may be used to immunize an animal against infection by *Streptococcus suis*.

14 Claims, 5 Drawing Sheets

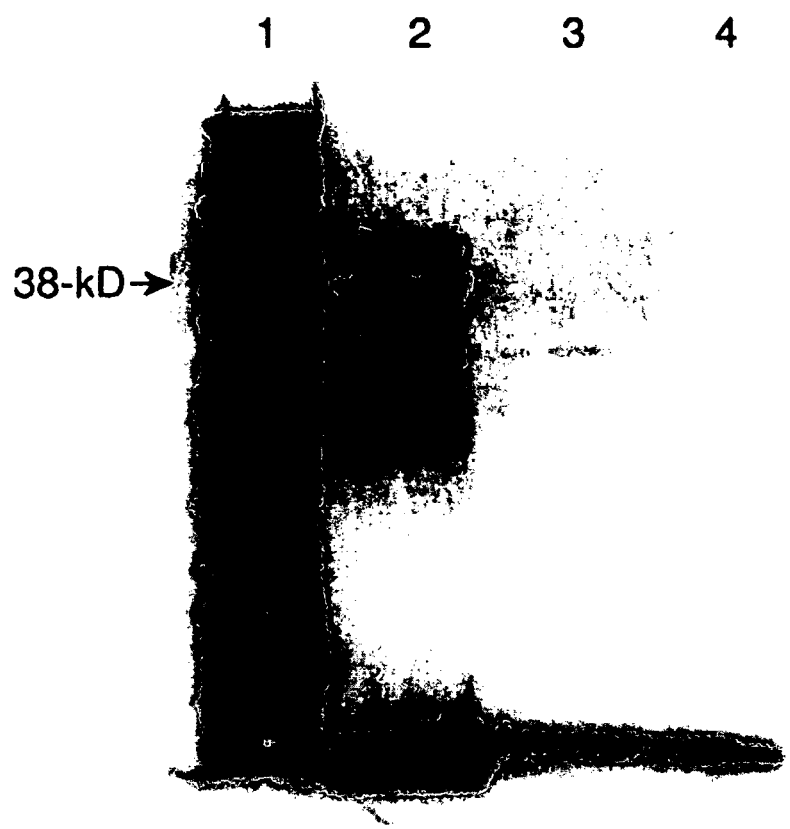
FIG. 1. Translation products of the plasmid carrying the gene encoding the 38-kDa protein.

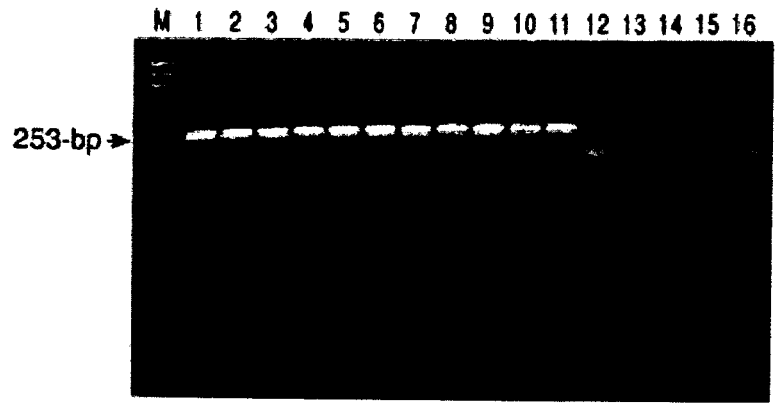
FIG. 2. Ethidium bromide-stained agarose gels of PCR products of 38-kDa protein nucleic acid.
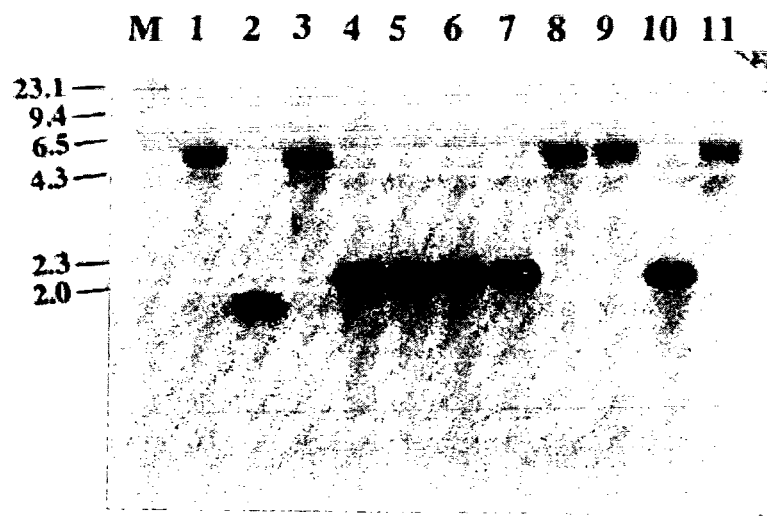
FIG. 3. Southern blot of chromosomal DNA from different strains of *S. suis* type 2.

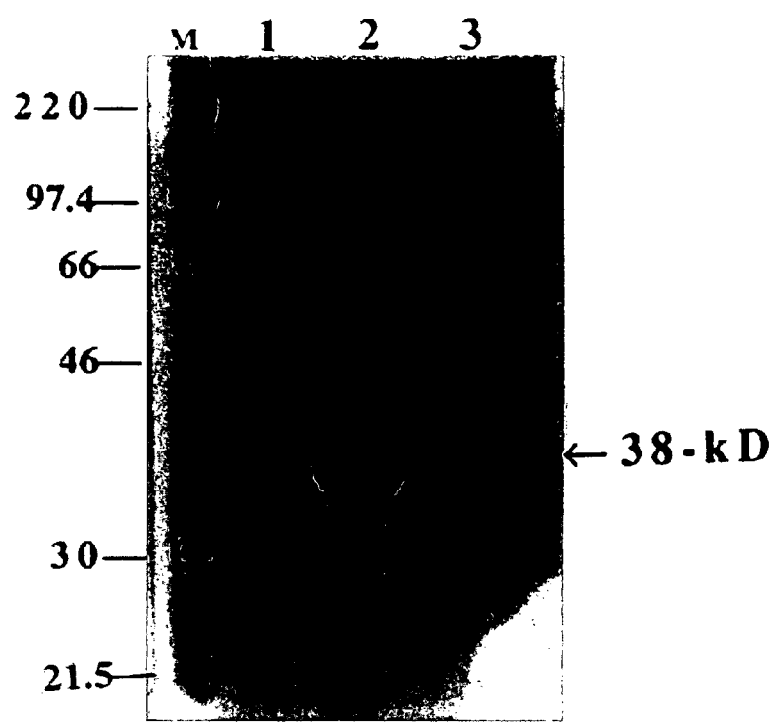
FIG. 4. Coomassie blue-stained SDS-polyacrylamide gel of the overexpressed and purified 38-kDa recombinant protein.

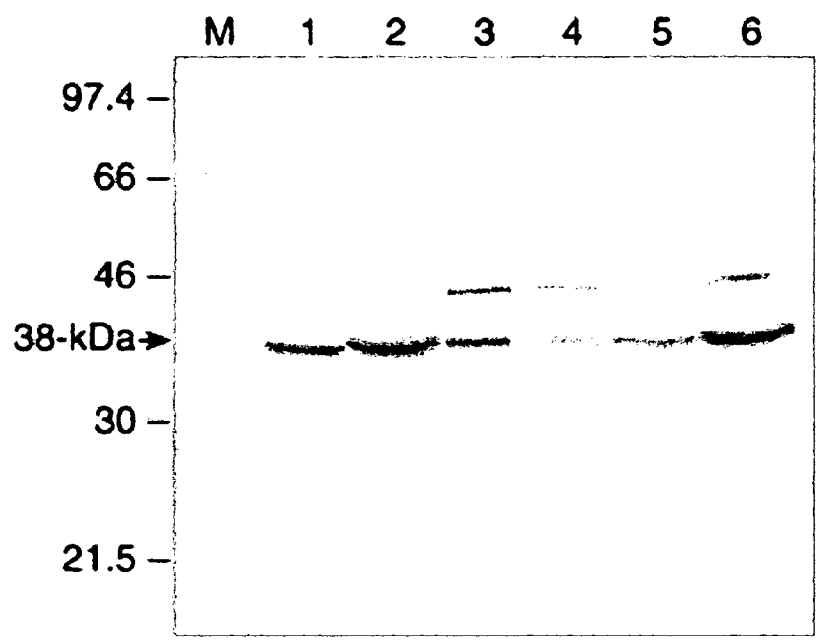
FIG. 5. Immunoblot (Western blot) analysis with polyclonal antibody raised against the purified recombinant 38-kDa protein.

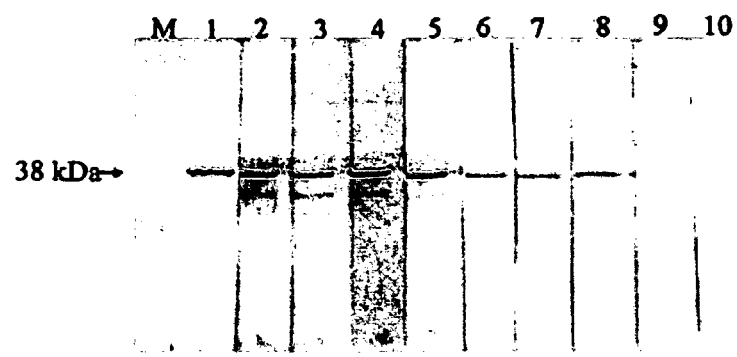
FIG. 6. Immunoblot analysis of pig sera and their reactivities against the purified recombinant 38-kDa protein.
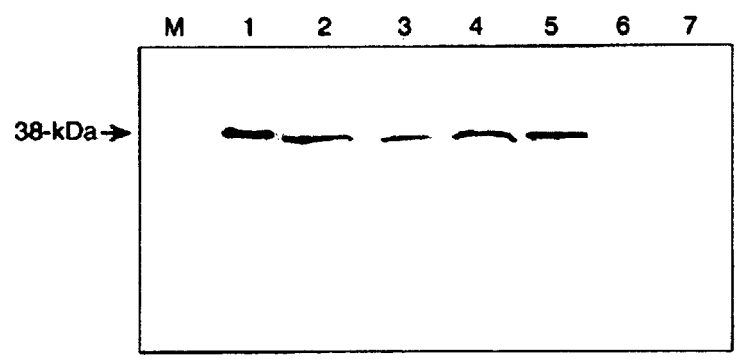
FIG. 7. Immunoblot analysis of proteins from cellular fractions of *S. suis* strain 1933.

USE OF *STREPTOCOCCUS SUIS* 38 KDA POLYPEPTIDE AS AN IMMUNOGEN

BACKGROUND

The present subject matter relates generally to the field of microbiology and immunology. In particular, the present subject matter relates to immunogenic compositions useful for inducing an immune response that may serve to protect an animal from infection by a pathogen. Reference is made herein to Okwumabua et al., CLIN DIAGN LAB. IMMUNOL. 2005, 12:484-490. All patents and publications cited herein are hereby incorporated herein by reference.

Microorganisms such as *Streptococcus* species are important swine pathogens. For example, *Streptococcus suis* causes many pathological conditions, such as arthritis, endocarditis, meningitis, polyserositis, and bronchopneumonia. *Streptococcus suis* also is an important zoonotic agent for people in contact with swine or their by-products and causes meningitis, permanent hearing loss, and septic shock. Thirty-five capsular types (types 1/2 and 1 to 34) are currently known. Type 2 is considered the type that is the most frequently associated with disease and is the type that is the most often isolated. Strains of other serotypes, such as serotypes 1/2, 7, 9, and 14, can also cause disease. Attempts to control the infection are hindered by a lack of thorough knowledge of the virulence factors and protective antigens of the bacterium, the existence of multiple serotypes with diverse genetic make-ups, and the evolution of multidrug-resistant strains.

Several protein components, including attenuated whole bacterial cells, have been evaluated as vaccines against *S. suis*. However, these studies did not achieve much success because the protection was either serotype or strain dependent, and in some instances the results were ambiguous. For example, Jacobs et al., (VET. REC. 139:225-228 (1996)), evaluated a suilysin-based subunit vaccine and showed that it conferred complete protection. However, the absence of suilysin in a substantial number of isolates recovered from diseased pigs hampers the use of this vaccine. Thus, identification of other antigenic factors will contribute to the development of a monovalent or a multivalent subunit vaccine that will protect pigs against infection by all capsular types.

In our effort to identify an *S. suis* gene(s) that may be involved in virulence and proteins that may be useful in the development of a reliable diagnostic reagent or vaccine to protect against infection with this bacterium, we identified a DNA region from a virulent strain of *S. suis* serotype 2 that encoded a polypeptide of 38 kDa. Of the 35 *S. suis* serotypes currently known, 31 contain and express the gene. The gene product was reactive with serum from pigs with *S. suis* infection, and the protein induced protective immunity in experimentally challenged pigs, making it a candidate for consideration in the development of a diagnostic reagent and vaccine.

SUMMARY

Disclosed herein is the use of polypeptides derived from microorganisms as immunogens. In some embodiments, the polypeptide is related to the 38 kDa polypeptide of a *Streptococcus* species (e.g., *Streptococcus suis*).

The methods disclosed herein may include inducing an immune response against one or more pathogens such as a species of *Streptococcus*. In some embodiments, the methods include inducing polyclonal antibodies against one or more pathogens that include a species of *Streptococcus* (e.g., *Streptococcus suis*) by administering to an animal a composition that includes an isolated 38 kDa polypeptide derived from a species of *Streptococcus* (e.g., 38 kDa polypeptide of *Streptococcus suis*). The animal may be a non-human animal (e.g., a swine). The methods disclosed herein also may include protecting an animal against infection by one or more pathogens that include a species of *Streptococcus* (e.g., *Streptococcus suis*) by administering to the animal a composition that includes an isolated 38 kDa polypeptide. For example, an animal (e.g., a non-human animal such as a swine) may be protected against infection by *Streptococcus suis* type 2 by administering to the animal a composition that includes an isolated 38 kDa polypeptide of *Streptococcus suis* and a suitable excipient.

Also disclosed are immunogenic compositions that may be useful for the disclosed methods. The immunogenic compositions may be monovalent or polyvalent. Typically, the immunogenic compositions include an isolated 38 kDa polypeptide of a species of *Streptococcus* (e.g., an isolated 38 kDa polypeptide of *Streptococcus suis*) and a suitable excipient. The 38 kDa polypeptide may be derived from *Streptococcus suis*, including *Streptococcus suis* of any capsular type such as type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34. In one suitable embodiment, the immunogenic composition includes an isolated 38 kDa polypeptide of *Streptococcus suis* type 2.

The immunogenic compositions may include polypeptides related to a 38 kDa polypeptide of a species of *Streptococcus*. For example, the immunogenic compositions may include an isolated polypeptide having at least about 95% amino acid sequence identity to an amino acid sequence of a 38 kDa polypeptide of a species of *Streptococcus* (e.g., *Streptococcus suis*). The reference 38 kDa polypeptide may be derived from *Streptococcus suis*, including any capsular type such as type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34.

In suitable embodiments, the immunogenic composition includes an isolated polypeptide having at least about 95% amino acid sequence identity to 38 kDa polypeptide of *Streptococcus suis* type 2. For example, the polypeptide may include SEQ ID NO:1 or a polypeptide having at least about 95% amino acid sequence identity to SEQ ID NO:1. The polypeptide may include a polypeptide encoded by SEQ ID NO:2. In some embodiments, the immunogenic composition may include a polypeptide encoded by a polynucleotide that hybridizes under stringent conditions to the complement of SEQ ID NO:2. Typically, the polypeptide is immunogenic. In some embodiments, the polypeptide may have a biological activity. For example, the polypeptide may have phosphoglycerate mutase activity.

The immunogenic composition may include a polypeptide that comprises one or more immunogenic fragments of 38 kDa polypeptide. For example, the polypeptide may comprise one or more epitopes of 38 kDa polypeptide. In some embodiments, the composition may include an isolated polypeptide which has at least a contiguous ten amino acid fragment of SEQ ID NO:1 (e.g., amino acid sequence 1-10 of SEQ ID NO:1, amino acid sequence 2-11 of SEQ ID NO:1, amino acid sequence 3-12 of SEQ ID NO:1, etc., . . . amino acid sequence 336-445 of SEQ ID NO:1.). Suitable fragments may include conserved fragments. Suitable fragment may include SEQ ID NO:3, SEQ ID NO:4, SEQ ID NO:5, SEQ ID NO:6, and SEQ ID NO:7. The polypeptide may include a fusion polypeptide (e.g., a fusion polypeptide that includes at least a portion of the polypeptide of SEQ ID NO:1). Typically, the polypeptide is immunogenic. In some embodiments, the polypeptide may have a biological activity (e.g., phosphoglycerate mutase activity).

The immunogenic compositions may be formulated for delivery in any suitable manner. For example, the immunogenic compositions may be formulated for at least one of intramuscular delivery, subdermal delivery, subcutaneous delivery, oral delivery, intravenous delivery, intraperitoneal delivery, and intranasal delivery.

The immunogenic compositions may include a polypeptide that has been modified to enhance immunogenicity. For example, the polypeptide may be conjugated to one or more haptens. The immunogenic compositions may include an adjuvant (e.g., a veterinarily acceptable adjuvant).

The immunogenic compositions typically include an isolated polypeptide at a concentration sufficient to induce an immunogenic response (e.g., antibody induction, a T-cell response, or both). The immunogenic compositions may include at least about 10 µg of the isolated polypeptide (or preferably, at least about 100 µg of the isolated polypeptide).

The immunogenic compositions may include a polypeptide related to 38 kDa polypeptide of a species of Streptococcus (e.g. Streptococcus suis) and may include at least one additional antigen of a pathogen (e.g., an antigen of a swine pathogen). In some embodiments, the immunogenic compositions may include at least one additional antigen of Streptococcus suis other than an antigen of 38 kDa polypeptide. In further embodiments, the immunogenic compositions include at least one additional antigen selected from the group consisting of an antigen of a Streptococcus species other than Streptococcus suis, an antigen of Mycoplasma spp., an antigen of Actinobacillus spp., an antigen of E. coli, an antigen of Helicobacter spp., an antigen of Salmonella spp., an antigen of Erysipelothrix spp., an antigen of Haemophilus spp., an antigen of Leptospira spp., an antigen of Clostridium spp., an antigen of Brachyspira spp., an antigen of Pasteurella spp., Bordetella spp., an antigen of Atrophic Rhinitis Virus, an antigen of Pseudorabies virus, an antigen of PRRS virus, an antigen or Hog cholera virur, an antigen of Swine Influenza, an antigen of Porcine Parvovirus, an antigen of Porcine Circovirus, an antigen of transmissible gastro-enteritis virus, and combinations thereof.

Also disclosed herein are kits. The kits may include one or more components for performing the methods disclosed herein. For example, the kits may include one or more of the immunogenic compositions disclosed herein or components for making the immunogenic compositions disclosed herein. The immunogenic compositions or components may be provided in any suitable form (e.g., liquid form or lyophilized form).

Also disclosed herein are isolated antisera, antibodies, or other binding molecules that specifically bind to 38 kDa polypeptide of a species of Streptococcus (e.g., Streptococcus suis) or to polypeptides related to 38 kDa polypeptide of a species of Streptococcus. The antisera, antibodies, or other binding molecules may specifically bind to 38 kDa polypeptide of Streptococcus suis or to a polypeptide related to 38 kDa polypeptide of Streptococcus suis. For example, the antisera, antibodies, or other binding molecules may specifically bind to a polypeptide having at least about 95% sequence identity to an amino acid sequence of 38 kDa protein of Streptococcus suis. Included are isolated antisera, antibodies, or other binding molecule that bind to the polypeptide of SEQ ID NO:1 or to a polypeptide having at least about 95% amino acid sequence identity to SEQ ID NO:1.

The isolated antibody may be of any suitable isotype (e.g., IgG, IgM, IgE, IgD, IgA, and mixtures thereof). The antibodies may be polyclonal or monoclonal. The antibodies or other binding molecule may be conjugated to a suitable label (e.g., a fluorophore, radioisotope, enzyme, and the like). The antibodies or other binding molecule may be modified for use in a diagnostic method.

Also disclosed herein are methods for detecting species, subspecies or types of a species of Streptococcus (e.g., Streptococcus suis) in a sample. The methods may include reacting the sample and an antibody that specifically binds to a 38 kDa polypeptide of a species of Streptococcus (e.g., Streptococcus suis, including the polypeptide of SEQ ID NO:1) to form a detectable complex. The methods may include reacting the sample and an antibody that specifically binds to a polypeptide having at least about 95% sequence identity to an amino acid sequence of a 38 kDa polypeptide of a species of Streptococcus (e.g., a polypeptide having at least about 95% sequence identity to 38 kDa polypeptide of Streptococcus suis, including the polypeptide of SEQ ID NO:1) to form a detectable complex.

The methods for detecting species, subspecies or types of Streptococcus (e.g., Streptococcus suis) in a sample may include detecting nucleic acid that encodes 38 kDa protein of a species of Streptococcus. For example, the methods may include amplifying nucleic acid that encodes 38 kDa protein of Streptococcus suis with suitable primers. Detecting nucleic acid may include hybridizing the nucleic acid with one or more specific probes. The primers or probes typically will specifically hybridize to the nucleic acid that encodes 38 kDa protein under high stringency conditions.

Also disclosed are methods of detecting antibodies against a species of Streptococcus (e.g., Streptococcus suis) in a sample. The methods typically include reacting the sample and 38 kDa polypeptide of a species of Streptococcus (e.g., 38 kDa polypeptide of Streptococcus suis, including a polypeptide of SEQ ID NO:1) to form a detectable complex. The methods may include reacting the sample and a polypeptide having at least about 95% sequence identity to an amino acid sequence of a 38 kDa protein of a species of Streptococcus (e.g., a polypeptide having at least about 95% sequence identity to a 38 kDa polypeptide of Streptococcus suis, including a polypeptide of SEQ ID NO:1) to form a detectable complex.

BRIEF DESCRIPTION OF THE DRAWINGS

FIG. 1. Translation products of the plasmid carrying the gene encoding the 38-kDa protein. An autoradiograph of the [$^{35}$S]methionine-labeled products synthesized in an E. coli K-12 extract and separated by SDS-PAGE is shown. Lanes: 1, products of a positive control (Promega, Madison, Wis.); 2, reactions of the gene template encoding the 38-kDa protein (pOT301); 3, reactions of the plasmid cloning vector pUC18 without the insert; 4, product of a control reaction with no template. The location of the ca. 38-kDa protein is indicated on the left. The molecular mass standard was very faint and as such was not labeled. The lower faint band in lane 2 was considered the plasmid cloning vector-coded protein since it is also present in lane 3.

FIG. 2. Example of ethidium bromide-stained agarose gels of PCR products with primers designed from the gene sequences encoding the 38-kDa protein. DNA from strains of serotypes 1/2 and 1 to 10 (lanes 1 to 11, respectively) and serotypes 20, 26, 32, and 33 (lanes 12 to 15, respectively) was used as the template. Lane M, HaeIII-digested φX174 DNA molecular mass markers (Promega, Madison, Wis.); lane 16, a negative control (no template). The expected migration of the amplicons is indicated on the left.

FIG. 3. Southern blot of chromosomal DNA from different strains of *S. suis* type 2 (lanes 1 to 11) digested with EcoRI and hybridized to the 1,170-bp EcoRV-HindIII fragment derived from the gene encoding the 38-kDa antigen. Lane M, digoxigenin-labeled molecular weight marker II (Boehringer Mannheim).

FIG. 4. Coomassie blue-stained SDS-polyacrylamide gel of the overexpressed and purified 38-kDa recombinant protein. The protein was overexpressed and purified as described previously. (Okwumabua, O. et al., 2001, CLIN. DIAGN. LAB. IMMUNOL. 8:251-257.) Lanes: M, rainbow molecular size marker (in kilodaltons); 1, whole-cell lysate of the uninduced pOT312 transformant of *E. coli* TOP10; 2, whole-cell lysate of the *E. coli* transformant with pOT312 following induction with arabinose; 3, recombinant protein purified from the pOT312 transformant of *E. coli* TOP10.

FIG. 5. Immunoblot (Western blot) analysis with polyclonal antibody raised against the purified recombinant 38-kDa protein showing expression of the gene encoding the 38-kDa protein by strains of other serotypes. Lanes: M, rainbow molecular size marker (in kilodaltons; Amersham); 1, purified recombinant 38-kDa protein; 2, whole-cell lysate of *S. suis* serotype 2 strain 1933; 3, whole-cell lysate of a serotype 1 strain; 4, whole-cell lysate of a serotype 1/2 strain; 5, whole-cell lysate of a serotype 7 strain; and 6, whole-cell lysate of a serotype 9 strain. The location of the 38-kDa protein is indicated by the arrow on the left. Other reactive bands (lanes 2 to 6) were considered *S. suis* protein bands that cross-reacted with the antibody.

FIG. 6. Immunoblot analysis of pig sera and their reactivities against the purified recombinant 38-kDa protein. Lanes: M, molecular size marker; 1 through 7, serum from pigs infected with *S. suis* type 2; 8, polyclonal antibody raised in a rabbit against the purified recombinant 38-kDa protein (positive control); 9, preimmune serum from the rabbit used to raise antibody against the purified protein (negative control); 10, preimmune serum from a pig prior to infection (negative control). Each lane is a strip cut from the membrane following Western transfer and prior to exposure to antibody.

FIG. 7. Immunoblot analysis of proteins from cellular fractions of *S. suis* strain 1933 with polyclonal antibody raised against the purified 38-kDa recombinant protein. Lanes: M, molecular size standard; 1, the purified 38-kDa protein (positive control); 2, cell wall fractions; 3, surface fractions; 4 and 5, cytoplasmic fractions; 6, periplasmic fraction; 7, cell-free culture supernatant.

DETAILED DESCRIPTION OF THE PREFERRED EMBODIMENTS

The terms "immunogenic composition" and "vaccine" are defined herein in a broad sense to refer to any type of biological agent in an administratable form capable of stimulating an immune response in an animal inoculated with the immunogenic composition or vaccine. An immune response may include induction of antibodies and/or induction of a T-cell response. Herein, the term "protection" when used in reference to an immunogenic composition or vaccine refers to the amelioration (either partial or complete) of any of the symptoms associated with the disease or condition in question. Thus, protection of animals from infection by a *Streptococcus* species such as *S. suis* by the present immunogenic compositions or vaccines generally results in a diminishing of bacterial growth and/or one or more of the clinical symptoms associated with infection by *Steptococcus* species (such as *S. suis*), including arthritis, endocarditis, meningitis, polyserositis, bronchopneumonia, meningitis, permanent hearing loss, and septic shock.

The methods disclosed herein may include inducing an immune response against one or more pathogens that include a species of *Streptococcus* (e.g., *Streptococcus suis*. For example, the methods may include inducing polyclonal antibodies against one or more pathogens that include a species of *Streptococcus* that may include *Streptococcus suis*. In some embodiments, the methods include administering to an animal a composition that includes a isolated polypeptide that is related to 38 kDa polypeptide of *Streptococcus suis*. As used herein the 38 kDa polypeptide of *S. suis* is the polypeptide encoded by the sequence referenced under GenBank accession number AF389083. (See SEQ ID NO:1 (polypeptide) and SEQ ID NO:2 (polynucleotide encoding polypeptide)).

A polypeptide related to 38 kDa polypeptide may include 38 kDa ploypeptide or a polypeptide having significant sequence identity to 38 kDa polypeptide. A polypeptide related to 38 kDa polypeptide may include a polypeptide having at least about 95% amino acid sequence identity to 38 kDa polypeptide (e.g., a polypeptide having at least about 95% amino acid sequence identity to a polypeptide of SEQ ID NO:1), which may be determined by methods known in the art (e.g., BLAST alignment). A polypeptide related to 38 kDa polypeptide may have deletions, insertions, or amino acid substitutions relative to 38 kDa polypeptide. Amino acid substitutions may include conservative amino acid substitutions (e.g., D<->E, K <->R, S<->T, and the like) or non-conservative amino acid substitutions. A polypeptide related to 38 kDa polypeptide may include an ortholog of 38 kDa polypeptide derived from *S. suis*, a 38 kDa polypeptide derived from another *Streptococcus* species (e.g., *Streptococcus pneumoniae* or *Streptococcus mutans*), or a 38 plypeptide derived from another genus of microorganism (e.g., *Lactococcus lactis, Listeria monocytogenes*, and *Clostridium perfringens*).

A polypeptide related to 38 kDa polypeptide may include a fusion polypeptide of 38 kDa polypeptide (e.g., biotinylated 38 kDa polypeptide). For example, a fusion polypeptide may include a fusion of 38 kDa polypeptide and another immunogenic polypeptide. A fusion polypeptide may include a fusion of 38 kDa polypeptide and a hapten. A polypeptide related to 38 kDa polypeptide may include a polypeptide that comprises one or more immunogenic fragments of 38 kDa polypeptide. For example, the polypeptide may comprise one or more epitopes of 38 kDa polypeptide. In some embodiments, the composition may include an isolated polypeptide which has at least a contiguous ten amino acid fragment of SEQ ID NO:1 (or a contiguous fifteen amino acid fragment of SEQ ID NO:1, a contiguous twenty amino acid fragment of SEQ ID NO:1, or a contiguous thirty amino acid fragment of SEQ ID NO:1). Suitable fragments may include conserved domains of SEQ ID NO:1. Suitable fragments may include one or more of SEQ ID NO:3, SEQ ID NO:4, SEQ ID NO:5, SEQ ID NO:6, and SEQ ID NO:7. Typically, the polypeptide related to 38 kDa polypeptide is immunogenic. In some embodiments, the polypeptide related to 38 kDa polypeptide may have a biological activity (e.g., phosphoglycerate mutase activity).

The methods disclosed herein may include administering an immunogenic composition to an animal. An "animal," as used herein, may include a mammal. An "animal," as used herein, may include a non-human animal (e.g., swine, cattle, horses, dogs, cats, and the like).

The methods disclosed herein also may include protecting an animal against infection by one or more pathogens that include a species of *Streptococcus* (e.g., *Streptococcus suis*) by administering to the animal a composition that includes an isolated 38 kDa polypeptide. The administered composition may include an immunogenic composition or a vaccine. For example, an animal (e.g., humans or a non-human animal such as a swine) may be protected against infection by *Streptococcus suis* type 2 by administering to the animal a composition that includes an isolated 38 kDa polypeptide of a *Streptococcus* species (e.g., 38 kDa polypeptide of *Streptococcus suis* type 2) and a suitable excipient. In some embodiments, the isolated 38 kDa polypeptide may be derived from a homologous microorganism, but the methods are not so limited. The 38 kDa polypeptide may be derived from *Streptococcus suis*, including *Streptococcus suis* of any capsular type such as type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34. In some suitable embodiments, the immunogenic composition includes an isolated 38 kDa polypeptide of *Streptococcus suis* type 2.

The immunogenic compositions may be monovalent or polyvalent. The immunogenic composition may include a polypeptide related to 38 kDa polypeptide of *Streptococcus suis* and may include at least one additional antigen of a pathogen (e.g., an antigen of a swine pathogen). In some embodiments, the immunogenic compositions may include at least one additional antigen of *Streptococcus suis* other than an antigen of 38 kDa polypeptide. In further embodiments, the immunogenic compositions include at least one additional antigen selected from the group consisting of an antigen of a *Streptococcus* species other than *Streptococcus suis*, an antigen of *Mycoplasma* spp. (e.g., *Mycoplasma hypopneumoniae*), an antigen of *Actinobacillus* spp. (e.g., *Actinobacillus pleuropneumoniae*), an antigen of *E. coli*, an antigen of *Helicobacter* spp., an antigen of *Salmonella* spp. (e.g., *Salmonella choleraesuis*), an antigen of *Erysipelothrix* spp. (e.g., *Erysipelothrix rhusiopathiae*), an antigen of *Haemophilus* spp. (e.g., *Haemophilus parasuis*), an antigen of *Leptospira* spp., an antigen of *Clostridium* spp., an antigen of *Brachyspira* spp., an antigen of *Pasteurella* spp. (e.g., *Pasteurella multiocida*), *Bordetella* spp. (e.g., *Bordetella bronchiseptica*), an antigen of Atrophic Rhinitis Virus, an antigen of Pseudorabies virus, an antigen of PRRS virus, an antigen or Hog cholera virus, an antigen of Swine Influenza, an antigen of Porcine Parvovirus, an antigen of Porcine Circovirus (e.g., *porcine circovirus* type II), an antigen of transmissible gastroenteritis (TGE) virus, and combinations thereof.

The immunogenic compositions may be formulated for delivery in any suitable manner. For example, the immunogenic compositions may be formulated for at least one of intramuscular delivery, subdermal delivery, subcutaneous delivery, oral delivery, intravenous delivery, intraperitoneal delivery, and intranasal delivery. 100361 The immunogenic compositions or vaccines can be administered using a variety of methods including intranasal and/or parenteral (e.g., intramuscular) administration. In some embodiments of the methods, the immunogenic composition or vaccine is administered intramuscularly one or more times at suitable intervals (e.g., at intervals of 2-4 weeks), followed by administration of the immunogenic composition or vaccine at least once intramuscularly or intranasally after a suitable time period (e.g., 2-4 weeks after the last parenteral administration of vaccine). The immunogenic compositions or vaccines may be administered to an animal of any suitable age. In some embodiments, the immunogenic compositions or vaccines are admistered to juvenile animals.

The present immunogenic composition or vaccines may include an adjuvant. For example, adjuvants may include vitamin E acetate solubilisate, aluminum hydroxide, aluminum phosphate or aluminum oxide, (mineral) oil emulsions, non-ionic detergents, squalene and saponins. Other adjuvants which may be used include an oil based adjuvants such as Freund's complete adjuvant (FCA), and Freund's incomplete adjuvant (FIA). Other adjuvants include cross-linked olefinically unsaturated carboxylic acid polymers, such as cross-linked acrylic acid polymers. As used herein the term "cross-linked acrylic acid polymer" refers to polymer and copolymers formed from a monomer mixture which includes acrylic acid as the predominant monomer in the mixture. Examples of suitable cross-linked acrylic acid polymers include those commercially available under the tradenames Carbopol® 934P and Carbopol® 971 (available from B.F.Goodrich Co., Cleveland, Ohio). Examples of suitable adjuvants include veterinarily accepted adjuvants.

It is generally advantageous to formulate the present compositions in dosage unit form for ease of administration and uniformity of dosage. "Dosage unit form" as used herein refers to physically discrete units suited as unitary dosages for the animal subjects to the treated; each unit containing a predetermined quantity of the active material calculated to produce the desired therapeutic effect in association with the required pharmaceutical carrier. The specification for the dosage unit forms are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 micrograms (preferably 100 micrograms) of an isolated polypeptide related to a 38 kDa polypeptide of a species of *Streptococcus* (e.g., a 38 kDa polypeptide of *S. suis*).

The present immunogenic composition and vaccines may be formulated with a pharmaceutically or veterinarily acceptable carrier. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

Sterile injectable solutions may be prepared by incorporating the isolated polypeptide related to 38 kDa in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It may also be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

Also disclosed herein are isolated antisera, antibodies, or other binding molecules that specifically bind to 38 kDa polypeptide of a species of *Streptococcus* (e.g., *Streptococcus suis*) or to polypeptides related to 38 kDa polypeptide of a species of *Streptococcus* (e.g., *Streptococcus suis*) For example, the antisera, antibodies, or other binding molecules, may include an isolated antibody that specifically binds to a polypeptide having at least about 95% sequence identity to an amino acid sequence of a 38 kDa protein of *Streptococcus suis*. Included are isolated antisera, antibodies, or other binding molecules that bind to the polypeptide of SEQ ID NO:1 or to a polypeptide having at least about 95% amino acid sequence identity to SEQ ID NO:1.

The isolated antibody or binding molecule may be of any suitable isotype (e.g., IgG, IgM, IgE, IgD, IgA, and mixtures thereof). The antibodies may be polyclonal or monoclonal. The antibodies or other binding molecules may be naturally occurring or synthetic (e.g., scFv). Other binding molecules may include antibody fragments (e.g., Fab fragments), coupled antibodies, and coupled antibody fragments. The antibodies or other specific binding molecules may be conjugated to a suitable label. Suitable labels may include fluorophores, such as but not limited to, fluorescein-type fluorophores, rhodamine-type fluorophores, green fluorescent protein and the like. Suitable labels may include radioisotopes, such as but not limited to $^3H$, $^{14}C$, $^{32}P$, $^{35}S$, $^{125}I$, and the like. Suitable labels may include enzymes, such as but not limited to horseradish peroxidase, alkaline phosphatase and the like. The antibodies may be modified for use in a diagnostic method.

Also disclosed herein are methods for detecting species, subspecies or types of *Streptococcus* species (e.g. *Streptococcus suis*) in a sample. The methods may include reacting the sample and an antibody that specifically binds to a 38 kDa polypeptide of a species of *Streptococcus* (e.g., 38 kDa polypeptide of *Streptococcus suis*, including the polypeptide of SEQ ID NO:1) to form a detectable complex. The antibody may be labeled. In some embodiments, the method include reacting the complex with a second antibody that recognizes the first antibody or that recognizes the 38 kDa polypeptide. The method may comprise a competitive type assay or a sandwich type assay. The assay may comprise a chromatographic lateral flow type assay. In some embodiments, one or more components of the assay may be immobilized to a solid support.

Also disclosed are methods of detecting antibodies against a species of *Streptococcus* (e.g., *Streptococcus suis*) in a sample. The methods typically include reacting the sample and a 38 kDa polypeptide of a species of *Streptococcus* (e.g., *Streptococcus suis*, including a polypeptide SEQ ID NO:1) to form a detectable complex. The 38 kDa polypeptide may be labeled. In some embodiments, the method include reacting the complex with a second antibody that recognizes the first antibody or that recognizes the 38 kDa polypeptide. The method may comprise a competitive type assay or a sandwich type assay. The assay may comprise a chromatographic lateral flow type assay. In some embodiments, one or more components of the assay may be immobilized to a solid support.

Also disclosed herein are methods for detecting species, subspecies or types of *Streptococcus* (e.g., *Streptococcus suis*) in a sample by detecting nucleic acid that encodes 38 kDa polypeptide. The methods may include reacting a sample with one or more oligonucleotides that are capable of specifically hybridizing to nucleic acid that encodes 38 kDa polypeptide (e.g., oligonucleotides that are capable of specifically hybridizing to nucleic acid that encodes 38 kDa polypeptide under stringent conditions). The oligonucleotide may be of any suitable length but typically is at least about 10 nucleotides (or desirably at least 15 nucleotide, or even more desirably at least about 20 nucleotides). The oligonucleotide may comprise a complement of the nucleic acid that encodes 38 kDa polypeptide or an oligonucleotide that has at least about 95% sequence identity to a complement of the nucleic acid that encodes 38 kDa polypeptide. The oligonucleotides may include primers (e.g., for PCR amplification) and/or probes. The oligonucleotides may be labeled to facilitate detection of nucleic acid that encodes 38 kDa polypeptide. For example, the oligonucleotides may be labeled with one or more dyes (e.g., fluorophores or quenchers).

Illustrated Embodiments

The subject matter disclosed herein may be illustrated by the following list of embodiments, which are presented to illustrate the present invention and to assist in teaching one of ordinary skill how to make and use the same. These embodiments are not intended in any way to narrow or otherwise limit the scope of the present invention.

One embodiment includes a method of inducing polyclonal antibodies against one or more pathogens that include *Streptococcus suis*, the method comprising administering to an animal a composition comprising an isolated 38 kDa polypeptide of *Streptococcus suis* and a suitable excipient.

The method of paragraph 48, wherein the animal is a non-human animal.

The method of paragraph 49, wherein the non-human animal is a swine.

The method of paragraph 48, wherein the isolated 38 kDa polypeptide of *Streptococcus suis* is derived from a capsular type of *Streptococcus suis* selected from the group consisting of type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34.

The method of paragraph 48, wherein the isolated 38 kDa polypeptide is derived from *Streptococcus suis* type 2.

The method of paragraph 48, wherein the composition comprises at least about 10 μg of the isolated polypeptide.

The method of paragraph 48, wherein the composition further comprises an adjuvant.

The method of paragraph 48, wherein the 38 kDa polypeptide is conjugated to a hapten.

The method of paragraph 48, wherein the polyclonal antibodies comprise neutralizing antibodies. 100571 The method of paragraph 48, wherein the composition is formulated for at least one of intramuscular delivery, subdermal delivery, subcutaneous delivery, oral delivery, intravenous delivery, intraperitoneal delivery, and intranasal delivery.

The method of paragraph 50, wherein the composition further comprises at least one additional antigen of a swine pathogen.

The method of paragraph 58, wherein the at least one additional antigen is an antigen selected from the group consisting of an antigen of a different *Streptococcus* species, an antigen of *Mycoplasma* spp., an antigen of *Actinobacillus* spp., an antigen of *Escherichia* spp., an antigen of *Helicobacter* spp., an antigen of *Salmonella* spp., an antigen of *Erysipelothrix* spp., an antigen of *Haemophilus* spp., an antigen of *Leptospira* spp., an antigen of *Clostridium* spp., an antigen of *Brachyspira* spp., an antigen of *Pasteurella* spp., *Bordetella* spp., an antigen of Atrophic Rhinitis Virus, an antigen of Pseudorabies virus, an antigen of PRRS virus, an antigen or Hog cholera virus, an antigen of Swine Influenza, an antigen of Porcine Parvovirus, an antigen of Porcine Circovirus, an antigen of transmissible gastro-enteritis virus, and combinations thereof.

One embodiment includes a method of inducing polyclonal antibodies against *Streptococcus suis* comprising administering to an animal a composition comprising an isolated polypeptide having at least about 95% amino acid sequence identity to a 38 kDa protein of *Streptococcus suis* and a suitable excipient.

The method of paragraph 60, wherein the isolated polypeptide has at least about 95% amino acid sequence identity to 38 kDa protein of *Streptococcus suis* type 2.

The method of paragraph 61, wherein the 38 kDa protein of *Streptococcus suis* type 2 comprises SEQ ID NO:1.

The method of paragraph 60, wherein the polypeptide has phosphoglycerate mutase activity.

One embodiment includes a method of protecting an animal against *Streptococcus suis* infection, the method comprising administering to the animal a composition comprising an isolated 38 kDa polypeptide of *Streptococcus suis* and a suitable excipient.

One embodiment includes an immunogenic composition comprising an isolated polypeptide having at least about 95% amino acid sequence identity to 38 kDa protein of *Streptococcus suis* and a suitable excipient.

The immunogenic composition of paragraph 65, wherein the composition is formulated for delivery to a swine.

One embodiment includes an isolated antibody that specifically binds to 38 kDa polypeptide of *Streptococcus suis*.

One embodiment includes an immunogenic composition comprising an isolated 38 kDa polypeptide of *Streptococcus suis* and a suitable excipient.

The immunogenic composition of paragraph 68, comprising an isolated 38 kDa polypeptide of *Streptococcus suis* selected from type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34.

The immunogenic composition of paragraph 68, comprising an isolated 38 kDa polypeptide of *Streptococcus suis* type 2.

One embodiment includes an immunogenic composition comprising an isolated polypeptide having at least about 95% sequence identity to an amino acid sequence of a 38 kDa protein of *Streptococcus suis*.

The immunogenic composition of paragraph 71, wherein the *Streptococcus suis* is selected from type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34.

The immunogenic composition of paragraph 72, wherein the *Streptococcus suis* is type 2.

One embodiment includes an immunogenic composition comprising an isolated polypeptide having at least about 95% sequence identity to an amino acid sequence of SEQ ID NO:1 and a suitable excipient.

The immunogenic composition of paragraph 74, wherein the polypeptide has the amino acid sequence of SEQ ID NO:1.

One embodiment includes an immunogenic composition comprising an isolated polypeptide which includes at least a contiguous ten amino acid fragment of SEQ ID NO:1 and a suitable excipient.

The immunogenic composition of paragraph 76, wherein the fragment comprises an amino acid sequence selected from the group consisting of amino acid sequence 1-10 of SEQ ID NO:1, amino acid sequence 2-11 of SEQ ID NO:1, amino acid sequence 3-12 of SEQ ID NO:1, etc. . . . amino acid sequence 336-445 of SEQ ID NO:1.

One embodiment includes an immunogenic composition comprising an isolated polypeptide which includes at least a contiguous twenty amino acid fragment of SEQ ID NO:1 and a suitable excipient.

The immunogenic composition of paragraph 78, wherein the fragment comprises an amino acid sequence selected from the group consisting of amino acid sequence 1-20 of SEQ ID NO:1, amino acid sequence 2-21 of SEQ ID NO:1, amino acid sequence 3-22 of SEQ ID NO:1, etc. . . . amino acid sequence 326-445 of SEQ ID NO:1.

The immunogenic composition of any of paragraphs 68-79, wherein the polypeptide is conjugated to a hapten.

The immunogenic composition of any of paragraphs 68-80, further comprising at least one adjuvant (desirably a veterinarily acceptable adjuvant).

The immunogenic composition of paragraph 81, wherein the composition comprises about 1-25% v/v of the adjuvant.

The immunogenic composition of any of paragraphs 68-82, wherein the composition comprises at least about 10 μg of the isolated polypeptide.

The immunogenic composition of paragraph 83, wherein the composition comprises at least about 100 μg of the isolated polypeptide.

The immunogenic composition of any of paragraphs 68-84, formulated for at least one of intramuscular delivery, subdermal delivery, subcutaneous delivery, oral delivery, intravenous delivery, intraperitoneal delivery, and intranasal delivery.

The immunogenic composition of any of paragraphs 68-85, further comprising at least one additional antigen of a swine pathogen.

The immunogenic composition of paragraph 86, wherein the at least one additional antigen is an antigen selected from the group consisting of an antigen of a different *Streptococcus* species, an antigen of *Mycoplasma* spp., an antigen of *Actinobacillus* spp., an antigen of *E. coli*, an antigen of *Helicobacter* spp., an antigen of *Salmonella* spp., an antigen of *Erysipelothrix* spp., an antigen of *Haemophilus* spp., an antigen of *Leptospira* spp., an antigen of *Clostridium* spp., an antigen of *Brachyspira* spp., an antigen of *Pasteurella* spp., *Bordetella* spp., an antigen of Atrophic Rhinitis Virus, an antigen of Pseudorabies virus, an antigen of PRRS virus, an antigen or Hog cholera virur, an antigen of Swine Influenza, an antigen of Porcine Parvovirus, an antigen of Porcine Circovirus, an antigen of transmissible gastro-enteritis virus, and combinations thereof.

One embodiment includes a method of inducing polyclonal antibodies against *Streptococcus suis* comprising administering the composition of any one of paragraphs 68-87 to an animal.

The method of paragraph 88, wherein the animal is a non-human animal.

The method of paragraph 89, wherein the non-human animal is a swine.

One embodiment includes a method of protecting an animal against *Streptococcus suis* infection comprising administering the composition of any one of paragraphs 68-87 to an animal.

One embodiment includes a method of protecting an animal against *Streptococcus suis* type 2 infection comprising administering the composition of any one of paragraphs 68-87 to an animal.

The method of paragraph 92, wherein the animal is a non-human animal.

The method of paragraph 93, wherein the non-human animal is a swine.

One embodiment includes a kit for inducing polyclonal antibodies against *Streptococcus suis*, the kit comprising an isolated 38 kDa polypeptide of *Streptococcus suis*.

One embodiment includes a kit for inducing polyclonal antibodies against *Streptococcus suis*, the kit comprising an isolated polypeptide having at least about 95% sequence identity to an amino acid sequence of a 38 kDa protein of *Streptococcus suis*.

One embodiment includes a kit for inducing polyclonal antibodies against *Streptococcus suis*, the kit comprising an isolated polypeptide having at least about 95% sequence identity to an amino acid sequence of SEQ ID NO:1.

The kit of any of paragraphs 95-97, further comprising at least one adjuvant (desirably a veterinarily acceptable adjuvant).

One embodiment includes an isolated antibody that specifically binds to a 38 kDa polypeptide of *Streptococcus suis*.

One embodiment includes an isolated antibody that specifically binds to a polypeptide having at least about 95% sequence identity to an amino acid sequence of a 38 kDa protein of *Streptococcus suis*.

One embodiment includes an isolated antibody that specifically binds to a polypeptide having at least about 95% sequence identity to amino acid sequence of SEQ ID NO:1.

One embodiment includes an isolated antibody that specifically binds to a polypeptide having an amino acid sequence of SEQ ID NO:1.

The isolated antibody of any of paragraphs 99-102, wherein the antibody is monoclonal.

One embodiment includes a diagnostic reagent for detecting *Streptococcus suis*, comprising the isolated antibody of any of paragraphs 99-103 and a label.

One embodiment includes a method of detecting *Streptococcus suis* in a sample, comprising reacting the sample and an antibody that specifically binds to a 38 kDa polypeptide of *Streptococcus suis* to form a detectable complex.

One embodiment includes a method of detecting *Streptococcus suis* in a sample, comprising reacting the sample and an antibody that specifically binds to a polypeptide having at least about 95% sequence identity to an amino acid sequence of a 38 kDa protein of *Streptococcus suis* to form a detectable complex.

One embodiment includes a method of detecting *Streptococcus suis* in a sample, comprising reacting the sample and an antibody that specifically binds to a polypeptide having at least about 95% sequence identity to amino acid sequence of SEQ ID NO:1 to form a detectable complex.

One embodiment includes a method of detecting *Streptococcus suis* in a sample, comprising reacting the sample and an antibody that specifically binds to a polypeptide having an amino acid sequence of SEQ ID NO:1 to form a detectable complex.

One embodiment includes a method of detecting antibodies against *Streptococcus suis* in a sample, comprising reacting the sample and a 38 kDa polypeptide of *Streptococcus suis* to form a detectable complex.

One embodiment includes a method of detecting antibodies against *Streptococcus suis* in a sample, comprising reacting the sample and a polypeptide having at least about 95% sequence identity to an amino acid sequence of a 38 kDa protein of *Streptococcus suis* to form a detectable complex.

One embodiment includes a method of detecting antibodies against *Streptococcus suis* in a sample, comprising reacting the sample and a polypeptide having at least about 95% sequence identity to amino acid sequence of SEQ ID NO:1 to form a detectable complex.

One embodiment includes a method of detecting antibodies against *Streptococcus suis* in a sample, comprising reacting the sample and a polypeptide having an amino acid sequence of SEQ ID NO:1 to form a detectable complex.

EXAMPLES

Bacterial strains, plasmids, and media. *S. suis* type 2 strain 1933, a virulent isolate, was used to construct the genomic library. Other *S. suis* isolates were recovered from pigs from diverse geographical locations. Plasmid pUC18, propagated in *Escherichia coli* DH5α, was used as the library expression vector; and pGEM (Promega, Madison, Wis.) was used for DNA sequencing. Luria-Bertani broth or agar was used to grow the *E. coli* strains. Todd-Hewitt medium supplemented with 0.6% yeast extract (Difco Laboratories, Detroit, Mich.) was used to grow the *S. suis* strains. When appropriate, ampicillin was used at 60 µg/ml for *E. coli* cultures. All cultures were incubated at 37° C.

Chemicals and enzymes. Enzymes were purchased from Promega or New England Biolabs (Beverly, Mass.) and were used as recommended by the manufacturer. Chemicals were purchased from Sigmna Chemical Co. (St. Louis, Mo.) or Fisher Scientific (Pittsburgh, Pa.). The digoxigenin-labeled DNA molecular-weight marker II and the digoxigenin-11-dUTP DNA-labeling kit and detection system were from Boehringer Mannheim (Indianapolis, Ind.). Serum samples were collected from seven pigs experimentally infected with virulent strains of *S. suis* type 2.

Construction and screening of a recombinant DNA library. *S. suis* DNA, which was extracted by a previously described method (Okwumabua, O. et al., 1995, J. CLIN. MICROBIOL. 33:968-972), was digested with the EcoRI restriction endonuclease. Restriction fragments were then size fractionated by agarose gel electrophoresis. Fragments in the size range of 1 to 23 kb were excised from the gel, purified by electroelution, and ligated into the pUC18 plasmid cloning vector that had been digested with EcoRI. The recombinant plasmids were transformed into E. coli DH5α by electroporation. Transformed cells were plated onto Luria-Bertani agar containing 60 µg of ampicillin per ml, isopropyl-β-D-thiogalactopyranoside (4 µl of a 20% solution), and 5-bromo-4-chlor-3-indolyl-β-D-galactopyranoside (40 µl of a 20-mg/ml solution) and grown at 37° C. overnight. The resulting white colonies were transferred to a fresh plate and were grown as described above. One loopful of each colony was solubilized in 100 µl of 1× sodium dodecyl sulfate (SDS) sample buffer by heating for 5 min at 100° C. The preparation was centrifuged for 2 min at 13,000×g to remove the cellular debris; and the cell-free lysate was used for Western blot analysis with a 1:500 dilution of polyclonal antibody raised against the whole-cell protein of S. suis type 2 as the primary antibody, followed by incubation in a 1:1,000 dilution of anti-rabbit immunoglobulin G (IgG) conjugated with horseradish peroxidase. The blots were developed with hydrogen peroxide and 4-chloro-1-naphthol. A colony designated DH5α (pOT301) was identified and characterized.

Nucleotide sequence determination and bioinformatics. The complete nucleotide sequences of both strands of the 2.0-kb EcoRI fragment in plasmid pOT301 were determined by the dideoxy-chain termination method with an automated nucleotide sequencer (Applied Biosystems, Foster City, Calif.). The nucleotide sequences and the deduced amino acid sequences were analyzed with MacVector software (Oxford Molecular Group, Inc., Campbell, Calif.). Searches for the similarity of the sequences with the sequences in GenBank were performed by using the BLAST network service.

PCR. Oligonucleotide primers were designed by using the 38-kDa gene sequence data. The sequences of the primers were 5'-ATGCCACGGATACCTTCCC-3' (SEQ ID NO: 10) (primer BAY46F) and 5'-CCGTCTCCTTAATGATCCGC-3' (SEQ ID NO: 11)(primer BAY46R). The primer pair was designed to amplify a 253-bp product from S. suis DNA. Amplification was performed with 100 ng of purified genomic DNA in a total volume of 50 µl containing 10 mM Tris-HCl (pH 8.3), 1.5 mM MgCl$_2$, 50 mM KCl, 0.00 1% gelatin, 200 µM each deoxynucleoside triphosphate (dATP, dCTP, dGTP, and dTTP), 1 µM each primer, and 2.5 U of Taq polymerase (Perkin-Elmer Corp., Norwalk, Conn.). The PCR assay was carried out in a Perkin-Elmer 2400 thermocycler, comprising 5 min of preincubation at 94° C., followed by 35 cycles of 1 min at 94° C., 1 min at 55° C., and 1 min at 72° C. A final extension was performed for 7 min at 72° C. The negative control was a reaction mixture containing all reagents but no DNA template. The PCR products were visualized by electrophoresis on a 0.8% agarose gel by standard procedures.

Electrophoresis and Southern blotting. Three micrograms of genomic DNA was digested with EcoRI, and the fragments were separated on a 0.8% agarose gel (Promega) and transferred to a nylon membrane (Boehringer Mannheim) by the method of Southern. After the fragments were transferred, the DNA was UV crossed-linked to the membrane (GS gene linker; Bio-Rad, Richmond, Calif.).

Probe preparation and hybridization. A 1,170-bp EcoRV-HindIII internal DNA fragment from pOT301 was labeled with digoxigenin-11-dUTP, according to the specifications of the manufacturer (Genius System; Boehringer Mannheim). Hybridization, washes, and hybrid detection were done according to the instructions provided with the Genius II nonradioactive labeling and detection kit (Boehringer Mannheim).

Analysis of the regions flanking the gene. To extend the known sequence beyond the EcoRi site flanking the gene, inverse PCR (IV-PCR) was performed with primers HP6 (5'-CTCGTCACGGGAAAACCATG-3') (SEQ ID NO: 12) and HP7 (5'-TGCTTCTTGGATACCTGCTG-3') (SEQ ID NO: 13). Chromosomal DNA from S. suis strain 1933 was restricted with HindIII and religated prior to IV-PCR. The PCR product was purified and sequenced with the same primers, and the nucleotide sequence was used to design primers that permitted analysis of DNA from isolates with different hybridization patterns.

Overexpression and purification of the recombinant 38-kDa protein. A 1,626-bp PCR fragment containing the open reading frame of the gene encoding the 38-kDa protein was obtained by amplification of pOT301 DNA with primers SF4 (5'-CGT GCA GAA CTT AGA AGC C-3', SEQ ID NO:8) and SR2 (5'-GAA TTC CTT CCT CAC CGA CC-3', SEQ ID NO:9) and cloned into the pCR 2.1 vector (Invitrogen, Carlsbad, Calif.) to create pOT308. To clone the 1,626-bp fragment in frame for overexpression, pOT308 was digested with the XhoI and KpnI restriction enzymes in combination to release the fragment. The fragment was then purified and ligated into the XhoI and KpnI sites of the pBAD/Myc-HisA expression vector to create pOT312. Plasmid pOT312 was transformed into E. coli TOP10 competent cells and overexpressed with arabinose according to the protocol of the manufacturer (Invitrogen). Following arabinose induction, the protein was purified as described previously (Okwumabua, O., et al., 2001, CLIN. DIAGN. LAB. IMMOL. 8:251-257).

Antigen and polyclonal antibody preparation. Polyclonal antibody against the recombinant protein was obtained by immunizing New Zealand White rabbits (Shelton's Bunny Bam Rabbits, Waverly Hall, Ga.) subcutaneously at multiple sites with approximately 200 µg of purified protein emulsified 1:1 with Freund complete adjuvant. The rabbits received one booster injection with the same antigen concentration emulsified 1:1 with Freund incomplete adjuvant 14 days later and were then bled 7 days after the booster was administered. The sera were filter sterilized and stored at −30° C. until they were used.

Western immunoblotting and in vitro transcription-translation experiments. Cell lysates, prepared as described above, were vacuum concentrated (15-fold), and 15 Al of sample was used for Western blot analysis. The proteins were reacted with a 1:500 dilution of the polyclonal antibody raised against the purified 38-kDa protein and then with a horseradish peroxidase-conjugated goat anti-rabbit IgG antibody (ICN) diluted 1:1,000. Bound antibodies were detected colorimetrically with hydrogen peroxide and 4-chloro-1-naphthol. To screen pig antisera for antibody against the 38-kDa antigen, a 1:100 dilution of the pig sera was used as the primary antibody, followed by the addition of a 1:1,000 dilution of alkaline phosphatase-conjugated affinity-purified anti-swine IgG (Rockland Immunochemicals, Gilbertsville, Pa.). The blots were developed with a 5-bromo-4-chloro-indolylphosphate-nitroblue tetrazolium salt mixture. For in vitro protein synthesis, 3 µg of purified plasmid DNA was added to an E. coli cell extract that contained [$^{35}$S]methionine and that was capable of coupled transcription-translation of exogenous DNA (Promega). The resulting translation products were separated by SDS-polyacrylamide gel electrophoresis (PAGE). After electrophoresis, the gel was dried and exposed to X-ray film (Kodak X-OMAT AR) at −70° C. for 2 days, and the film was developed in a Kodak film processor.

Cellular location of the 38-kDa protein. The surface, cell wall, cytoplasmic, and periplasmic protein fractions of *S. suis* were prepared by previously described methods (Mercurio, A. et al., 1985, MOL. GEN. GENET. 200:472-475; Shimoji, Y. et al., 1999, INFECT. IMMUN. 67:1646-1651; Tavares, F. et al., 2000, J. MICROBIOL. METHODS 30:171-178), and analyzed by Western blotting with a polyclonal antibody directed against the purified 38-kDa antigen.

Animals, immunization, and challenge. Ten pigs (age, 3 weeks; average weight, 14 lb) were purchased from the Auburn University Swine Facility, Auburn, Ala.

The ears of the pigs were tagged with colored numbers for identification purposes and the pigs were divided into two groups of five pigs each. The first group of pigs (red tag; identification numbers 43, 44, 45, 46, and 47) consisted of the vaccination group, and the second group (blue tag; identification numbers 92, 93, 94, 95, and 96) consisted of the control group. Prior to administration of the first dose of vaccine, serum (preimmune) was collected from all animals and screened to rule out the presence of serum antibodies against *S. suis*. The pigs in the first group were then vaccinated intramuscularly at two injection sites in the neck with 1 ml of vaccine preparations emulsified in Freund complete adjuvant. Each animal received approximately 100 µg of the purified recombinant 38-kDa protein-based vaccine, and the second group of pigs (pigs 92, 93, 94, 95, and 96) received a placebo composed of physiological saline in adjuvant (negative control). Two weeks after the initial vaccination, serum was collected from all pigs for antibody screening; and the pigs received a booster of the same vaccine preparations by the same route, but this time the vaccine was emulsified 1:1 with Freund incomplete adjuvant. Fourteen days after administration of the booster, serum was again collected from the pigs, followed by intravenous challenge in the ear vein with 1.5× $10^6$ CFU of an overnight culture of the homologous *S. suis* serotype 2 strain. The pigs were monitored twice daily for clinical signs of disease.

Nucleotide sequence accession number. The GenBank accession number for the 38-kDa protein sequence of *S. suis* is AF389083.

Identification of the 38-kDa protein. The gene library yielded a colony designated *E. coli* DH5α(pOT301) that produced a 38-kDa protein which reacted faintly with a polyclonal antibody, which was raised in rabbit cells, against the whole-cell protein of *S. suis* type 2 (data not shown). Because of the poor reactivity of the antibody to the protein, an in vitro protein synthesis experiment was performed to verify gene expression and to confirm the size of the gene product. The result confirmed that the gene is expressed and that the size of the product is 38 kDa. (See FIG. 1). Restriction analysis localized the gene within a 2.0-kb EcoRI fragment, and expression was orientation dependent in the pUC18 cloning vector.

Nucleotide and deduced amino acid sequence analysis. Analysis of the nucleotide sequence revealed that it contained three open reading frames (ORFs) of sufficient sizes to code for the 38-kDa polypeptide observed by the immunoblotting and the in vitro protein synthesis experiments (See FIG. 1. See also FIG. 5). The first ORF starts at position 479, the second ORF starts at position 512, and the third ORF starts at position 551. All three ORFs end in the termination codon TAA at position 1814. Proximal to the 5' end of the ORF are regions that resemble the consensus ribosome binding site and the −10 and −35 promoter sequences. The first ATG at nucleotide 479 is probably the start of translation, because it is preceded six nucleotides upstream by a hexanucleotide (AGGAGA) that is the putative ribosome binding site. The G+C content of the gene is 47.5 mol %, which is in close agreement with that reported for *S. suis* (38 to 42%).

The sequence of the protein that is predicted from the DNA sequence and that starts at the first in-frame ATG codon (position 479) consists of 445 amino acid residues with a calculated molecular mass of 46.4 kDa, in contrast to the 38 kDa estimated in the Western blotting and in vitro experiments. (See FIG. 1. See also FIG. 5). No signal sequence was noted, as determined by a hydropathy plot; and the protein had an estimated isoelectric point of 4.7. Several regions of high hydrophobicity, in comparison to regions of hydrophilicity, were observed on the hydropathy plots. Analysis of the deduced amino acid sequence of the protein revealed the absence of tryptophan.

A search of the GenBank database revealed that the sequences shared 83% identity at the nucleotide level to a gene of unknown function from the complete genome sequence of *Streptococcus pneumoniae*. At the amino acid level, the deduced primary sequence shared homology with those of unknown function from *S. pneumoniae* (89%), *Streptococcus mutans* (86%), *Lactococcus lactis* (80%), *Listeria monocytogenes* (74%), and *Clostridium perfringens* (64%).

PCR and hybridization. To demonstrate that the cloned fragment originated from *S. suis* and to examine the extent of conservation of the gene among the *S. suis* capsular types, PCR primers whose sequences were derived from the nucleotide sequence of the cloned fragment were used to amplify the DNA of the native *S. suis* strains encompassing all serotypes. The primers amplified the DNA from strains of most serotypes and produced a fragment of the expected size. DNA from strains belonging to serotypes 20, 26, 32, and 33 was nonreactive to the primers, as evidenced by the lack of an amplicon on agarose gels. (See FIG. 2). Because insufficient homology at the primer binding regions could result in the lack of amplification, we used hybridization experiments following EcoRI digestion to verify the PCR results. On the basis of the results of the analysis of our cloned fragment, digestion with the enzyme would produce a 2.0-kb fragment that would hybridize to the probe whose sequence was derived from within the gene. The results of the PCR and the hybridization methods were in agreement, suggesting that the cloned fragment originated from *S. suis* and that the gene is absent from strains of some serotypes. Unlike PCR, the hybridization studies revealed the existence of restriction fragment length differences that separated the strains into three genetic groups on the basis of the resulting fragment sizes of approximately 1.8, 2.0, and 5.0 kb, respectively. (See FIG. 3).

Molecular basis for restriction fragment length differences. To determine the genetic basis for the differences in the restriction fragment lengths, IV-PCR was performed to sequence the regions beyond the EcoRI fragment that contained the gene. The results revealed a base pair substitution (in boldface) at the EcoRI recognition sequence (GAATTC to GGATTC) at the 3' end of the gene in isolates that gave a 5-kb band in the hybridization studies. (See FIG. 3, lanes 1, 3, 8, 9, and 11). The basis for the 1.8-kb fragment was not determined. (See FIG. 3, lane 2) Because it is smaller than the expected 2.0-kb fragment, the fragment probably resulted from a deletion event.

Construction and overexpression of the 38-kDa protein. To produce a sufficient quantity of the protein for antibody production, the cloned fragment was inserted in frame into the pBAD/Myc-His version A expression vector (Invitrogen) as described above, overexpressed, and gel purified. The purified protein gave a prominent 38-kDa band and was used to generate polyclonal antibody in rabbit cells. (See FIG. 4).

Reactivity of antibody produced against the 38-kDa recombinant protein. In order for the recombinant protein to serve as a candidate for the development of a diagnostic reagent, it must be immunogenic and the antibody produced against the protein must be reactive with a similar protein from a wild-type S. suis strain(s). FIG. 5 shows the reactivities of proteins from whole-cell lysates of wild-type S. suis strains to a polyclonal antibody raised against the purified recombinant protein. A protein from the wild-type strains reacted with the antibody and had a molecular mass identical to that of the recombinant protein. Other reactive bands were considered S. suis proteins that cross-reacted with the antibody. FIG. 6 shows the reactivities of serum samples from pigs experimentally infected with S. suis type 2 strains to the 38-kDa recombinant protein. All samples produced a detectable signal against the antigen. These results demonstrate that the recombinant protein was not altered, that the gene encoding the protein is expressed in infected animals, and that the product is immunogenic. Thus, the results illustrate the potential use of the recombinant protein in the development of a serodiagnostic assay for the detection of S. suis infection. Isolates of the serotypes that were positive by the PCR and the hybridization studies expressed the protein, as determined by immunoblotting. The protein was not detected in the PCR- and hybridization-negative serotypes (serotypes 20, 26, 32, and 33). (See Table 1). This result indicates the antigenic conservation of the protein among the strains of the serotypes that carry the gene.

TABLE 1

Expression of the gene encoding the 38-kDa antigen by strains of different S. suis capsular types, as determined by immunoblot analysis

| S. suis Serotype | No. of Strains Tested | No. of Strains Positive for: | |
|---|---|---|---|
| | | Gene by PCR and Hybridization | 38-kDa Protein by Immunoblotting |
| 1 | 6 | 6 | 6 |
| 1/2 | 3 | 3 | 3 |
| 2 | 23 | 23 | 23 |
| 3 | 1 | 1 | 1 |
| 4 | 1 | 1 | 1 |
| 5 | 1 | 1 | 1 |
| 6 | 1 | 1 | 1 |
| 7 | 2 | 2 | 2 |
| 8 | 1 | 1 | 1 |
| 9 | 1 | 1 | 1 |
| 10 | 1 | 1 | 1 |
| 11 | 1 | 1 | 1 |
| 12 | 1 | 1 | 1 |
| 13 | 1 | 1 | 1 |
| 14 | 1 | 1 | 1 |
| 15 | 1 | 1 | 1 |
| 16 | 1 | 1 | 1 |
| 17 | 1 | 1 | 1 |
| 18 | 1 | 1 | 1 |
| 19 | 1 | 1 | 1 |
| 20 | 1 | 0 | 0 |
| 21 | 1 | 1 | 1 |
| 22 | 1 | 1 | 1 |
| 23 | 1 | 1 | 1 |
| 24 | 1 | 1 | 1 |
| 25 | 1 | 1 | 1 |
| 26 | 1 | 0 | 0 |
| 27 | 1 | 1 | 1 |
| 28 | 1 | 1 | 1 |
| 29 | 1 | 1 | 1 |
| 30 | 1 | 1 | 1 |
| 31 | 1 | 1 | 1 |
| 32 | 1 | 0 | 0 |
| 33 | 1 | 0 | 0 |
| 34 | 1 | 1 | 1 |

Cellular location of the 38-kDa protein. Surface-exposed and cell wall-associated proteins of bacteria are, in general, targets for vaccine development or the production of a serodiagnostic reagent. Western blot analysis was performed with S. suis cell extracts to determine the structural location of the 38-kDa protein. The polyclonal antibody produced against the purified protein reacted to cell wall, surface, and cytoplasmic proteins; and its size was identical to that of the purified recombinant protein. No reactivity was observed in the periplasmic extract or the growth medium (See FIG. 7).

Protective value of the recombinant protein. Because the protein was immunogenic in pigs and the antibody produced against the protein reacted with a protein of identical size from the wild-type strains of S. suis, as indicated in FIG. 5, we endeavored to determine its protective capability in an animal challenge model. None of the serum samples obtained from any of the experimental pigs reacted with the purified 38-kDa protein at the start of the experiment (day 0). The lack of reactivity with the protein indicated that the pigs had not previously been exposed to 38-kDa protein-positive strains of S. suis. In group 1 (vaccinated group), two of the five pigs (pigs 44 and 47) showed easily detectable antibodies against the protein 2 weeks postvaccination, while three pigs (pigs 43, 45, and 46) gave weak antibody responses (See Table 2).

TABLE 2

Production of antibody against the 38-kDa antigen by individual pigs and antibody reactivity with the antigen, as determined by Western blot analysis

| Animal No. | Reactivity on day[a]: | | | Group |
|---|---|---|---|---|
| | 0 | 14 | 28 | |
| 43 | − | ± | + | Vaccinated |
| 44 | − | ++ | ++++ | Vaccinated |
| 45 | − | ± | +++ | Vaccinated |
| 46 | − | ± | + | Vaccinated |
| 47 | − | ++ | +++ | Vaccinated |
| 92 | − | − | − | Control group |
| 93 | − | − | − | Control group |
| 94 | − | − | − | Control group |
| 95 | − | − | − | Control group |
| 96 | − | − | − | Control group |

[a] ±, weak reactivity; +, moderate reactivity; ++, good reactivity; +++, strong reactivity; ++++, very strong reactivity; −, no reactivity.

Two weeks after administration of the booster dose (day 28), three of the five pigs (pigs 44, 45, and 47) had high titers of antibody against the protein, while two of the animals had moderate titers. Throughout this period no reactivity of the antibody with the protein was detected with sera from pigs in the control group. (See Table 2). These results confirm that the protein is immunogenic in pigs and that the level of antibody production is dependent on the particular animal.

Three of the five pigs vaccinated with physiological saline in adjuvant (the control group) died as a result of the infection 2 to 4 days after the challenge. The remaining two animals were sick by recovered with time. (See Table 3).

TABLE 3

Mortality rate among pigs immunized with the S. suis 38-kDa recombinant protein following challenge with a homologous S. suis type 2 strain

| Group No. | Treatment | No. of Pigs Sick/No. of Pigs Injected | No. of Pigs Dead/No. of Pigs Injected | % Mortality |
|---|---|---|---|---|
| 1 | Control | 5/5 | 3/5 | 60 |
| 2 | 38-kDa recombinant protein vaccine | 1/5 | 0/5 | |

Specific clinical signs of disease, such as lameness, nervousness, and incoordination, were frequently recorded in the control group. Nonspecific clinical signs of disease, such as depression and a lack of appetite, were also observed. The pigs' body temperatures and leukocyte counts were also increased. In contrast, pigs in the vaccinated group were completely protected against challenge with a strain of a homologous serotype. (See Table 3). Only one of the pigs in this group showed temporary clinical signs, which consisted of arthritis and depression. These findings indicated that the S. suis recombinant 38-kDa protein could be a good candidate for consideration in the development of a recombinant subunit vaccine for the prevention of S. suis diseases in pigs.

Discussion. Several criteria can be used to identify antigens that can be useful in the development of a serodiagnostic reagent for the detection of S. suis infection or antigens which have the potential to elicit a cross-protective immune response against S. suis. First, the antigen should be present in at least all pathogenic strains of S. suis, regardless of their serotype. Second, antibody against the antigen should be present in infected animals, indicating that it is immunogenic and is expressed during infection.

This report describes the identification and characterization of the gene encoding a 38-kDa protein from a virulent strain of S. suis type 2, strain 1933. Characterization of the gene product showed that it is immunogenic in swine infected with pathogenic strains of S. suis type 2 as well as in swine vaccinated with the purified protein and provided protection against challenge with a strain of a homologous serotype. The protein was detected in S. suis cell wall and surface extracts and shares properties with the native protein. For example, a polyclonal antibody raised against the recombinant protein recognized the native protein from S. suis type 2, and the recombinant and native proteins had identical molecular masses. (See FIG. 5). The size similarity of the recombinant and native proteins and the reactivity between the recombinant and native proteins indicate that the recombinant protein was not altered in E. coli.

In an in vitro gene expression system, the cloned gene directed the production of a ca. 38-kDa polypeptide. This molecular mass is consistent with that observed by Western blotting with polyclonal antibody directed against the purified recombinant protein, but different from the calculated molecular mass of 46.4 kDa derived from the deduced amino acid sequence. The size disparity may be due to protein processing or anomalous migration of this primarily hydrophobic protein in SDS-polyacrylamide gels. It is also possible that the lack of a bulky amino acid residue such as tryptophan may influence the mobility of the protein in the gel.

The expression of the cloned gene in E. coli in the plasmid cloning vector pUC18 is orientation dependent, because in the reverse orientation the protein could not be detected on Western blots or in an in vitro gene expression system (data not shown). Thus, the cloned gene is probably not expressed from its own promoter, or it may contain a promoter that did not function in E. coli. In this case, expression is probably under the control of the ampicillin resistance gene promoter in the pUC18 cloning vector.

Surface-exposed and cell wall-associated proteins of bacteria are, in general, targets for vaccine development or the production of serodiagnostic reagents. In this study, the 38-kDa antigen was detected in the cell wall, surface, and cytoplasmic fractions. We were therefore unable to conclude where the protein is located by the techniques that we used. However, cross contamination between fractions cannot be ruled out. A different approach is therefore needed to solve this problem.

The GenBank database is a useful source for the prediction of protein function. A search of the database revealed that the deduced primary sequence of the 38-kDa protein shared homology with sequences of unknown function in some gram-positive bacteria. We were therefore unable to use the database to assign a putative function to the protein. Nonetheless, it is safe to assume that the protein serves a common function in gram-positive bacteria. Work is under way in an effort to determine its function.

A recombinant subunit vaccine (suilysin) that confers protection in pigs has been reported previously. However, the usefulness of the vaccine was limited because the target protein is absent from a large number of S. suis strains isolated from diseased pigs. In another study, purified muramidase-released protein and extracellular factor reportedly conferred protection in experimentally challenged pigs. However, most of the S. suis serotype 2 strains isolated from diseased pigs in Canada were negative for muramidase-released protein and extracellular factor. In this study, we tested strains from various geographical locations, including the United States, Canada, and Europe. Except for strains of serotypes 20, 26, 32, and 33, which lack the gene and which, as a result, do not produce the protein, strains of all other S. suis serotypes, regardless of their origins, contain the gene and express the 38-kDa protein. Strains of S. suis serotypes 1/2, 1, 2, 7, 9, and 14 are the most commonly associated with disease, with type 2 being the most significant. Strains of serotypes 20, 26, 32, and 33 are clinically insignificant and as such are not of major concern at present. Thus, the 38-kDa antigen has the potential for use in the development of a mono- or multivalent vaccine to protect against S. suis diseases.

Genetic heterogeneity can be a result of a mutation, insertion of a genetic element, or a deletion. Because genetic heterogeneity has previously been demonstrated in S. suis strains, we were interested in determining the molecular basis for the restriction fragment length differences observed in this study. Although point mutations are rare events, we noted that a point mutation in the EcoRI recognition sequence located 190 bp from the stop codon of the gene encoding the 38-kDa antigen was the basis for the differences. This mutation likely resulted in EcoRI cutting at the next site downstream in the isolates that yielded the 5.0-kb fragment.

CONCLUSION

In our continued effort to search for a *Streptococcus suis* protein(s) that can serve as a vaccine candidate or a diagnostic reagent, we constructed and screened a gene library with a polyclonal antibody raised against the whole-cell protein of *S. suis* type 2. A clone that reacted with the antibody was identified and characterized. Analysis revealed that the gene encoding the protein was localized within a 2.0-kbp EcoRI DNA fragment. The nucleotide sequence contained an open reading frame that encoded a polypeptide of 445 amino acid residues with a calculated molecular mass of 46.4 kDa. By in vitro protein synthesis and Western blot experiments, the protein exhibited an electrophoretic mobility of approximately 38 kDa. At the amino acid level the deduced primary sequence shared homology with sequences of unknown function from *Streptococcus pneumoniae* (89%), *Streptococcus mutans* (86%), *Lactococcus lactis* (80%), *Listeria monocytogenes* (74%), and *Clostridium perfringens* (64%). Except for strains of serotypes 20, 26, 32, and 33, Southern hybridization analysis revealed the presence of the gene in strains of other *S. suis* serotypes and demonstrated restriction fragment length differences caused by a point mutation in the EcoRI recognition sequence. We confirmed expression of the 38-kDa protein in the hybridization-positive isolates using specific antiserum against the purified protein. The recombinant protein was reactive with serum from pigs experimentally infected with virulent strains of *S. suis* type 2, suggesting that the protein is immunogenic and may serve as an antigen of diagnostic importance for the detection of most *S. suis* infections. Pigs immunized with the recombinant 38-kDa protein mounted antibody responses to the protein and were completely protected against challenge with a strain of a homologous serotype, the wild-type virulent strain of *S. suis* type 2, suggesting that it may be a good candidate for the development of a vaccine that can be used as protection against *S. suis* infection. Analysis of the cellular fractions of the bacterium by Western blotting revealed that the protein was present in the surface and cell wall extracts. The functional role of the protein with respect to pathogenesis and whether antibodies against the antigen confer protective immunity against diseases caused by strains of other pathogenic *S. suis* capsular types remains to be determined.

REFERENCES

Arends, J. P., and H. C. Zanen. 1988. Meningitis caused by *Streptococcus suis* in humans. Rev. Infect. Dis. 10:131-137.

Ferretti, J. J., and R. Curtis III (ed.). 1987. Compilation of nucleotide sequences that signal the initiation of transcription and translation of streptococci, p. 293. In *Streptococcal genetics*. American Society for Microbiology, Washington, D.C.

Gottschalk, M., P. Turqeon, R. Higgins, M. Beaudoin, and A. M. Bourgault. 1991. Susceptibility of *Streptococcus suis* to penicillin. J. Vet. Diagn. Investig. 3:170-172.

Gottschalk, M., A. Lebrun, H. J. Wisselink, J. D. Dubreuil, H. E. Smith, and U. Vecht. 1998. Production of virulence related-proteins by Canadian strains of *Streptococcus suis* capsular type 2. Can. J. Vet. Res. 62:75-79.

Graves, M. C., and J. C. Rabinowitz. 1986. In vivo and in vitro transcription of the *Clostridium pasteurianum* ferrodoxin gene. J. Biol. Chem. 261:11409-11415.

Hampson, D. J., D. T. Trott, I. L. Clarke, C. G. Mwaniki, and I. D. Robertson. 1993. Population structure of Australian isolates of *Streptococcus suis*. J. Clin. Microbiol. 31:2895-2900.

Higgins, R., M. Gottschalk, M. Beaudoin, and S. A. Rawluk. 1992. Distribution of *Streptococcus suis* capsular types in Quebec and western Canada. Can. Vet. J. 33:27-30.

Holt, M. E., M. R. Enright, and T. J. L. Alenxander. 1988. lmmunization of pigs with live cultures of *Streptococcus suis* type 2. Res. Vet. Sci. 45:349-352.

Holt, M. E., M. R. Enright, and T. J. L. Alexander. 1990. Protective effect of sera raised against different fractions of *Streptococcus suis* type 2. J. Comp. Pathol. 103:85-94.

Jacobs, A. A. C., A. J. G. van den Berg, and P. L. W. Loeffen. 1996. Protection of experimentally infected pigs by suilysin, the thiol-activated haemolysin (suilysin) of *Streptococcus suis*. Vet. Rec. 139:225-228.

Kilper-Balz, R., and K. H. Schleifer. 1987. *Streptococcus suis* sp. nov., nom. rev. Int. J. Syst. Bacteriol. 37:160-162.

Mercurio, A., and P. A. Manning. 1985. Cellular localization and export of the soluble haemolysin of *Vibrio cholerae* El Tor. Mol. Gen. Genet. 200:472-475.

Okwumabua, O., J. Staats, and M. M. Chengappa. 1995. Detection of genomic heterogeneity in *Streptococcus suis* isolates by DNA restriction fragment length polymorphisms of rRNA genes (ribotyping). J. Clin. Microbiol. 33:968-972.

Okwumabua, O., O. Abdelmagid, and M. M. Chengappa. 1999. Hybridization analysis of the gene encoding a hemolysin (suilysin) of *Streptococcus suis* type 2: evidence for the absence of the gene in some isolates. FEMS Microbiol. Lett. 181:113-121.

Okwumabua, O., J. S. Persaud, and P. G. Reddy. 2001. Cloning and characterization of the gene encoding the glutamate dehydrogenase of *Streptococcus suis* serotype 2. Clin. Diagn. Lab. Ihmunol. 8:251-257.

Robertson, I. D., and D. K Blackmore. 1989. Prevalence of *Streptococcus suis* types 1 and 2 in domestic pigs in Australia and New Zealand. Vet. Rec. 124:391-394.

Sambrook, J., and D. W. Russell. 2001. Molecular cloning: a laboratory manual, 3rd ed. Cold Spring Harbor Laboratory Press, Cold Spring Harbor, N.Y.

Sanger, F., S. Nicklen, and A. R. Coulson. 1977. DNA sequencing with chain-terminating inhibitors. Proc. Natl. Acad. Sci. USA 74:5463-5467.

Segers, R. P. A. M., T. Kenter, L. A. M. Haan, and A. A. C. Jacobs. 1998. Characterisation of the gene encoding suilysin from *Streptococcus suis* and expression in field strains. FEMS Microbiol. Lett. 167:255-261.

Shimoji, Y., Y. Mori, and V. A. Fishetti. 1999. Immunological characterization of a protective antigen of *Erysipelothrix rhusiopathiae:* identification of the region responsible for protective immunity. Infect. Immun. 67:1646-1651.

Shine, J., and J. Dalgarno. 1974. The 3'-terminal sequence of *Escherichia coli* 16S ribosomal RNA: complementary to non-sense triplets and ribosome binding sites. Proc. Natl. Acad. Sci. USA 71:1342-1346.

Shnerrson, J. M., B. Chattopadhyay, M. F. G. Murphy, and I. W. Fawcett. 1980. Permanent perceptive deafness due to *Streptococcus suis* type II infection. J. Laryngol. Ontol. 94:425-427.

Southern, E. M. 1975. Detection of specific sequences among DNA fragments separated by gel electrophoresis. J. Mol. Biol. 98:503-517.

Staats, J. J., I. Feder, O. Okwumabua, and M. M. Chengappa. 1997. *Streptococcus suis:* past and present. Vet. Res. Commun. 21:381-407.

Staats, J. J., B. L. Plattner, J. Nietfield, S. Dritz, and M. M. Chengappa. 1998. Use of ribotyping and hemolysin activity to identify highly virulent *Streptococcus suis* type 2 isolates. J. Clin. Microbiol. 36:15-19.

Tavares, F., and A. Sellstedt. 2000. A simple, rapid and non-destructive procedure to extract cell wall-associated proteins from Frankia. J. Microbiol. Methods 30:171-178.

Wisselink, H. J., U. Vecht, N. Stockhofe-Zurwieden, and H. E. Smith. 2001. Protection of pigs against challenge with virulent *Streptococcus suis* serotype 2 strains by a muramidase released protein and extracellular factor vaccine. Vet. Rec. 148:473-477.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

What is claimed is:

1. An immunogenic composition comprising an isolated polypeptide having at least 95% amino acid sequence identity to SEQ ID NO:1 and a suitable excipient, wherein the composition comprises an effective amount of the isolated polypeptide for inducing an immune response that protects against *Streptococcus suis* infection.

2. The immunogenic composition of claim 1, wherein the isolated polypeptide is from a capsular type of *Streptococcus suis* selected from the group consisting of type 1, type 1/2, type 2, type 3, type 4, type 5, type 6, type 7, type 8, type 9, type 10, type 11, type 12, type 13, type 14, type 15, type 16, type 17, type 18, type 19, type 21, type 22, type 23, type 24, type 25, type 27, type 28, type 29, type 30, type 31, and type 34.

3. The immunogenic composition of claim 2, wherein the isolated polypeptide of *Streptococcus suis* is from capsular type 2.

4. The immunogenic composition of claim 1, wherein the isolated polypeptide consists of SEQ ID NO:1.

5. The immunogenic composition of claim 1, wherein the composition comprises at least about 10 μg of the isolated polypeptide.

6. The immunogenic composition of claim 1, wherein the composition further comprises an adjuvant.

7. The immunogenic composition of claim 1, wherein the polypeptide is conjugated to a hapten.

8. The immunogenic composition of claim 1, wherein the composition is formulated for at least one of intramuscular delivery, subdermal delivery, subcutaneous delivery, oral delivery, intravenous delivery, intraperitoneal delivery, and intranasal delivery.

9. The immunogenic composition of claim 1, wherein the composition further comprises at least one additional antigen of a swine pathogen.

10. The immunogenic composition of claim 9, wherein the at least one additional antigen is an antigen selected from the group consisting of an antigen of a different *Streptococcus* species, an antigen of *Mycoplasma* spp., an antigen of *Actinobacillus* spp., an antigen of *Escherichia* spp., an antigen of *Helicobacter* spp., an antigen of *Salmonella* spp., an antigen of *Erysipelothrix* spp., an antigen of *Haemophilus* spp., anantigen of *Leptospira* spp., an antigen of *Clostridium* spp., an antigen of *Brachyspira* spp., an antigen of *Pasteurella* spp., *Bordetella* spp., an antigen of Atrophic Rhinitis Virus, an antigen of Pseudorabies virus, an antigen of PRRS virus, an antigen or Hog cholera virus, an antigen of Swine Influenza, an antigen of Porcine Parvovirus, an antigen of Porcine Circovirus , an antigen of transmissible astroenteritis virus, and combinations thereof.

11. The immunogenic composition of claim 1, wherein the composition is formulated for delivery to non-human animal.

12. The immunogenic composition of claim 11, wherein the non-human animal is a swine.

13. A method of protecting an animal against *Streptococcus suis* infection, the method comprising administering the composition of claim 1 to an animal.

14. The method of claim 13, wherein the animal is a swine.

* * * * *

SEQUENCE LISTING

```
<160> NUMBER OF SEQ ID NOS: 13

<210> SEQ ID NO 1
<211> LENGTH: 445
<212> TYPE: PRT
<213> ORGANISM: Streptococcus suis

<400> SEQUENCE: 1

Met Asp Ile Arg Gln Val Arg Glu Thr Ile Glu Met Ile Glu Glu Gln
 1               5                  10                  15

Asn Phe Asp Ile Arg Thr Ile Thr Met Gly Ile Ser Leu Leu Asp Cys
            20                  25                  30

Ile Asp Ser Asp Ile Asp Lys Ala Ala Glu Lys Val Tyr Thr Lys Ile
        35                  40                  45

Val Thr Lys Ala Lys Asn Leu Val Ala Val Gly Asp Glu Ile Ala Ala
    50                  55                  60

Glu Leu Gly Leu Pro Ile Val Asn Lys Arg Val Ser Val Thr Pro Ile
65                  70                  75                  80

Ala Leu Ile Gly Ala Ala Thr Asp Ala Thr Asp Tyr Leu Pro Leu Ala
                85                  90                  95

His Ala Leu Asp Lys Ala Ala His Glu Ile Gly Ile Asp Phe Ile Gly
           100                 105                 110

Gly Phe Ser Ala Leu Ala Gln Lys Gly Tyr Gln Lys Gly Asp Glu Ile
       115                 120                 125

Leu Ile Asn Ser Ile Pro Gln Ala Leu Ala Gln Thr Ser Lys Val Cys
   130                 135                 140

Ser Ser Val Asn Ile Gly Ser Thr Lys Thr Gly Ile Asn Met Thr Ala
145                 150                 155                 160

Val Arg Asp Met Gly Arg Ile Ile Lys Glu Thr Ala Glu Ala Ser Asp
                165                 170                 175

Met Gly Ala Ala Lys Leu Val Val Phe Ala Asn Ala Val Glu Asp Asn
           180                 185                 190

Pro Phe Met Ala Gly Ala Phe His Gly Val Gly Glu Ala Asp Val Val
       195                 200                 205

Ile Asn Val Gly Val Ser Gly Pro Gly Val Val Lys Arg Ala Leu Glu
   210                 215                 220

Lys Val Arg Gly Glu Ser Phe Asp Val Val Ala Glu Thr Val Lys Lys
225                 230                 235                 240
```

```
Thr Ala Phe Lys Ile Thr Arg Ile Gly Gln Leu Val Gly Asn Met Ala
                245                 250                 255

Ser Glu Arg Leu Gly Val Lys Phe Gly Ile Val Asp Leu Ser Leu Ala
            260                 265                 270

Pro Thr Pro Ala Val Gly Asp Ser Val Ala Arg Val Leu Glu Glu Met
        275                 280                 285

Gly Leu Glu Thr Val Gly Thr His Gly Thr Thr Ala Ala Leu Ala Leu
    290                 295                 300

Leu Asn Asp Ala Val Lys Lys Gly Val Met Ala Cys Asn Gln Val
305                 310                 315                 320

Gly Gly Leu Ser Gly Ala Phe Ile Pro Val Ser Glu Asp Glu Gly Met
                325                 330                 335

Ile Ala Ala Val Gln Asn Gly Ser Leu Asn Leu Glu Lys Leu Glu Ala
            340                 345                 350

Met Thr Ala Ile Cys Ser Val Gly Leu Asp Met Ile Ala Ile Pro Glu
        355                 360                 365

Thr Thr Pro Ala Glu Thr Ile Ala Ala Met Ile Ala Asp Glu Ala Ala
    370                 375                 380

Ile Gly Val Ile Asn Gln Lys Thr Thr Ala Val Arg Ile Ile Pro Leu
385                 390                 395                 400

Gly Lys Glu Gly Asp Met Ile Glu Phe Gly Gly Leu Leu Gly Thr Ala
                405                 410                 415

Pro Val Met Lys Val Asn Gln Ala Ser Ser Val Asp Phe Ile Asn Arg
            420                 425                 430

Gly Gly Gln Ile Pro Ala Pro Ile His Ser Phe Lys Asn
        435                 440                 445

<210> SEQ ID NO 2
<211> LENGTH: 2503
<212> TYPE: DNA
<213> ORGANISM: Streptococcus suis

<400> SEQUENCE: 2
gaattcggtg acactagtgt atcacagact ggtagaaata gaaagtttgt aacttaaaaa    60
ttaggcaact ctagccgtag ccgaatagaa gaaacagttg gagttgtaaa cacgtacgat   120
acaggtagaa atcaaaagat ttttaccttt ttctgtctat ttatgataaa atatatgaaa   180
atttagaaga ggtgttcaga tgaaagctat tgttacagtt gtcggtaagg acaagtcagg   240
aattgttgcg ggtgttgcga ccaagattgc ggagttaggg ctcaatatcg atgatatttc   300
acaaactgtt ttggatgagt attttaccat gatggcggtg gtgtcgtcag atgagaagaa   360
agatttcacc aagcttcgtg cagaacttag aagcctatgg tcaggctttg aatgtgaaaa   420
tcaacattca aagtgcagcc attttttgatg ctatgcacaa cttgtaagga gagatttcat   480
ggatattaga caggttagag aaaccattga aatgattgag gagcagaatt tcgatattcg   540
gaccatcacc atggggattt ccctcttgga ctgtatcgac tcggatatcg acaaggctgc   600
ggagaaagtg tataccaaga ttgtcaccaa ggccaagaac ttggtagcag tcggcgatga   660
gattgcggca gaactaggac ttcccattgt caacaaacgg tgtcagtaa cgcctattgc   720 tttgattggt gcggcgacgg atgccacgga ttaccttccc ctagctcatg ccttggacaa   780
ggcggctcat gagatcggca tcgattttat cggtggtttt tcagctcttg ctcaaaaggg   840
ctaccaaaaa ggtgatgaaa tcctcatcaa ctctattccg caggcattgg cccaaacctc   900
taaggtctgc tcgtcagtca atatcggctc gaccaagacg ggtatcaata tgacggctgt   960
```

-continued

```
gcgggacatg gggcggatca ttaaggagac ggcggaggct tctgatatgg gggctgccaa    1020
gttggtggtc tttgccaatg cggttgagga caatcctttc atggcggggg ccttccacgg    1080
tgtcggcgag gcggatgtgg tcatcaatgt cggcgtgtct gggcctggtg tggtcaagcg    1140
tgcccttgaa aaagtgcgtg gtgagagctt tgatgtggtg gcggagaccg tcaagaagac    1200
ggctttcaag attaccgta tcggtcagtt ggtcggcaat atggccagtg aacgcctggg    1260
ggttaagttc ggtatcgtgg acctgtcgct tgctccaaca ccagctgttg gcgactcagt    1320
agcacgggtt ttggaggaaa tgggcttaga aaccgttggt acgcacggaa cgactgctgc    1380
cctggctttg ctcaatgacg cagtcaaaaa gggtggggtc atggcctgca accaagtcgg    1440
tggcttgtca ggtgccttta tccctgtgtc tgaggatgag ggcatgattg cggcggtgca    1500
aaatggctcg ctcaaccttg aaaaattgga agccatgacg gctatctgtt ctgtaggttt    1560
ggacatgatt gccattccag aaacaacgcc tgctgaaacc attgcggcta tgattgcgga    1620
tgaagcggct attggggtta tcaatcagaa aacaactgcg gttcgtatta ttccgcttgg    1680
aaaagaagga gacatgattg aatttggcgg ccttctggga acagctcctg ttatgaaggt    1740
caatcaagct tcgtctgtgg actttatcaa ccgtggtggt cagattccag caccgattca    1800
tagctttaag aactaaaaaa cgtagaccga ttgccacaag cagtcggttt tttgttatac    1860
taatagtaag aaatgacaag gagaaaaacg aatggcagat gtaagattat atatttctcg    1920
tcacgggaaa accatgttca ataccattgg gcgcgtgcag ggctggtgtg atacgccgct    1980
gaccaaggtc ggtgaggaag gaattcgtga actgggcttg gggctcaagg atgcgggcct    2040
tgactttaaa ctagccgtat ccagtgatct gggtcgaacc gttcagacca tgaccatcgc    2100
ccagcgtgag ttaggaattt tagggaaaat cccttattac aagacaagc gtatccgtga    2160 atggtgtttc ggtagttttg aaggcatgta cgatgccgag cttttccaag gggtcctgcc    2220
tcgtttgaaa gggacagttg atgcgacggg tatgtccttt gcggaaatcg cagcaggtat    2280
ccaagaagca gacaccgctg gctgggcgga atcgtgggag gttttgagca accgtatctt    2340
gacaggtttt gaatccatcg cccaggactt ggaaaaacaa ggcggaggca atgcccttgt    2400
ggtcagccac ggtatgacta ttgcgacatt ggctcatttg ttagagccag agcgtggtgc    2460
caatgtcttt ctcgataacg gctcaatcac cgtcctcaaa tac                      2503
```

<210> SEQ ID NO 3
<211> LENGTH: 16
<212> TYPE: PRT
<213> ORGANISM: Streptococcus suis

<400> SEQUENCE: 3

Val Cys Ser Ser Val Asn Ile Gly Ser Thr Lys Thr Gly Ile Asn Met
 1               5                  10                  15

<210> SEQ ID NO 4
<211> LENGTH: 16
<212> TYPE: PRT
<213> ORGANISM: Streptococcus suis

<400> SEQUENCE: 4

Ala Lys Leu Val Val Phe Ala Asn Ala Val Glu Asp Asn Pro Phe Met
 1               5                  10                  15

<210> SEQ ID NO 5
<211> LENGTH: 13
<212> TYPE: PRT
<213> ORGANISM: Streptococcus suis

```
<400> SEQUENCE: 5

Val Ile Asn Val Gly Val Ser Gly Pro Gly Val Val Lys
 1               5                  10

<210> SEQ ID NO 6
<211> LENGTH: 20
<212> TYPE: PRT
<213> ORGANISM: Streptococcus suis

<400> SEQUENCE: 6

Gly Thr Thr Ala Ala Leu Ala Leu Leu Asn Asp Ala Val Lys Lys Gly
 1               5                  10                  15

Gly Val Met Ala
             20

<210> SEQ ID NO 7
<211> LENGTH: 18
<212> TYPE: PRT
<213> ORGANISM: Streptococcus suis

<400> SEQUENCE: 7

Val Gly Gly Leu Ser Gly Ala Phe Ile Pro Val Ser Glu Asp Glu Gly
 1               5                  10                  15

Met Ile

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgtgcagaac ttagaagcc                                              19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaattccttc ctcaccgacc                                             20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgccacgga ttaccttccc                                             20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
ccgtctcctt aatgatccgc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgtcacgg gaaaaccatg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgcttcttgg atacctgctg                                              20
```